United States Patent [19]

Murase et al.

[11] Patent Number: 5,130,002
[45] Date of Patent: Jul. 14, 1992

[54] METHOD OF PROCESSING OXYGEN CONCENTRATION SENSOR BY APPLYING AC CURRENT, AND THE THUS PROCESSED SENSOR

[75] Inventors: Takao Murase, Kohnan; Tsunenori Yoshimura, Nagoya, both of Japan

[73] Assignee: NGK Insulators, Ltd., Japan

[21] Appl. No.: 610,799

[22] Filed: Nov. 8, 1990

[30] Foreign Application Priority Data

Nov. 15, 1989 [JP] Japan .................. 1-296625

[51] Int. Cl.$^5$ .................. G25F 7/00; G01N 27/26
[52] U.S. Cl. .................. 204/153.16; 204/424; 204/425; 204/406; 204/427; 204/153.1; 204/426
[58] Field of Search .................. 204/406, 426, 427, 421, 204/153.1, 153.16, 425, 424; 123/349, 429, 440, 489, 510; 60/273, 276, 277

[56] References Cited

U.S. PATENT DOCUMENTS

| | | | |
|---|---|---|---|
| 4,419,190 | 12/1983 | Dietz et al. | 204/425 |
| 4,505,804 | 3/1985 | Mase et al. | 204/426 |
| 4,863,583 | 9/1989 | Kurachi et al. | 204/426 |
| 4,882,033 | 11/1989 | Shibata et al. | 204/426 |
| 4,950,380 | 8/1990 | Kurosawa et al. | 204/426 |

FOREIGN PATENT DOCUMENTS 59-190652 10/1984 Japan .

Primary Examiner—John Niebling
Assistant Examiner—Bruce Bell
Attorney, Agent, or Firm—Parkhurst, Wendel & Rossi

[57] ABSTRACT

A method of processing a sensing element of an oxygen sensor including an oxygen-ion conductive solid electrolyte, an electrochemical oxygen pumping cell having a first and a second electrode disposed on the solid electrolyte, an electrochemical oxygen sensing cell having a third and a fourth electrode disposed on the solid electrolyte, and diffusion-resistance means for introducing an external measurement gas for contact with the second and third electrodes. An alternating current having a frequency of not higher than 10 Hz is applied to at least one of the oxygen pumping and sensing cells, with the sensing element held at 600° C. or higher, to form minute cracks on the surface of each metal grain of the first and second electrodes and/or third and fourth electrodes. The alternating current is 1-5 times as large as a polarographic limit current value of the corresponding pumping and sensing cells.

10 Claims, 4 Drawing Sheets

METHOD OF PROCESSING OXYGEN CONCENTRATION SENSOR BY APPLYING AC CURRENT, AND THE THUS PROCESSED SENSOR

BACKGROUND OF THE INVENTION

1. Field of the Invention

The present invention relates to a method of processing a sensing element of an oxygen concentration sensor, to effectively improve stability in the sensing accuracy, and the oxygen concentration sensor having the thus processed sensing element.

2. Discussion of the Prior Art

A sensor which uses an oxygen-ion conductive solid electrolyte such as a zirconia ceramic and which operates according to the principle of an oxygen concentration cell is known as an oxygen concentration sensor for determining the oxygen concentration of a measurement gas such as a combustion gas within an industrial boiler or an exhaust gas emitted by an internal combustion engine.

Laid-open Publication No. 59-190652 of unexamined Japanese patent application shows an example of such an oxygen concentration sensor of a so-called double-cell type, which is capable of dealing with both an oxidizing measurement gas and a reducing measurement gas. This double-cell type oxygen sensor has an electrochemical oxygen sensing cell and an electrochemical oxygen pumping cell which are formed as an integral sensing element. The oxygen sensing cell has an internal measurement gas space into which a measurement gas is introduced from an external space under a suitably predetermined diffusion resistance. The sensing cell includes a measuring electrode exposed to the measurement gas in the internal measurement gas space, and a reference electrode exposed to a reference gas. An electromotive force is induced between the measuring and reference electrodes, according to the principle of an oxygen concentration cell. The oxygen pumping cell is operated by a controlled pumping current applied thereto, to effect an oxygen pumping action for controlling the oxygen concentration within the internal measurement gas space to which the measuring electrode is exposed, so that the electromotive force inducted by the oxygen sensing cell coincides with a predetermined value. The oxygen concentration of the measurement gas (state of the oxidizing or reducing atmosphere) is determined based on the level of the pumping current at which the electromotive force coincides with the predetermined value.

Theoretically, the oxygen concentration of the measurement gas is represented by the pumping current applied to the pumping cell in the double-cell type oxygen concentration sensor as described above. In practical use of the sensor, however, the detected pumping current does not accurately reflect the oxygen concentration of the measurement gas. Namely, the sensor suffers from some measuring error, or a fluctuation in the output characteristic, and is not satisfactory in the stability of measuring accuracy.

It is also noted that the theoretical or notional relationship between the oxygen concentration of the measurement gas and the detected pumping current of the pumping cell is greatly influenced by the temperature of the sensing element of the sensor. That is, the output characteristic of the sensor tends to vary with the temperature. Further, the output characteristic easily changes when the measurement gas contains CO, $H_2O$ or other substances which easily adhere to the sensing element.

On the other hand, there is recently an increasing requirement for improved operating stability of such oxygen concentration sensor, in the field of controlling an internal combustion engine of a motor vehicle, keeping pace with an increasing requirement for improved accuracy of detecting the air/fuel ratio of an air-fuel mixture supplied to the engine. Thus, there exists a need for improvement in the known oxygen concentration sensor as described above.

SUMMARY OF THE INVENTION

It is a first object of the present invention to provide a method of processing a sensing element of a double-cell type oxygen concentration sensor, for effectively improving the operating or measuring stability, without increasing the structural complexity and/or cost of manufacture of the sensor.

A second object is to provide a double-cell type oxygen concentration sensor which assures improved operating stability or improved stability in the measuring accuracy with consistent output characteristic.

The first object may be achieved according to one aspect of the present invention, which provides a method of processing a sensing element of an oxygen concentration sensor including an electrochemical oxygen pumping cell having an oxygen-ion conductive first solid electrolyte layer, and a first and a second electrode disposed on the first solid electrolyte layer, an electrochemical oxygen sensing cell having an oxygen-ion conductive second solid electrolyte layer and a third and a fourth electrode disposed on the second solid electrolyte layer, and diffusion-resistance means for introducing an external measurement gas under a predetermined diffusion resistance, for contact with the second and third electrodes, the method comprising a step of applying an alternating current having a frequency of not higher than 10 Hz to at least one of the oxygen pumping and sensing cells of said sensing element, through the first and second electrodes, and/or through the third and fourth electrodes, while the sensing element is held at a temperature not lower than 600° C. The alternating current is determined to be 1–5 times as large as a polarographic limit current value of the corresponding cell.

As a result of applying the alternating current to the oxygen pumping cell and/or the oxygen sensing cell, according to the present method, the metal grains of the electrodes of the processed electrochemical cell or cells, have minute cracks on their surfaces, thereby providing a sufficiently large number of points of contact (so-called triple contact points) among the electrode material, solid electrolyte material and measurement gas, at the interface between the electrodes and the solid electrolyte layer. Accordingly, the output characteristic of the sensing element of the sensor is effectively stabilized under varying operating condition, assuring improved stability in the accuracy of measurement or determination of the oxygen concentration of the measurement gas by the sensor, without increasing the structural complexity and/or cost of manufacture of the sensor.

The above advantage may be enhanced when the alternating current is applied between the first and second electrodes of the oxygen pumping cell concurrently when the alternating current is applied between the third and fourth electrodes of said oxygen sensing cell. The application of the alternating current to the cell or cells may be preferably and easily effected while the sensing element is placed in the ambient atmosphere.

For effectively processing the sensing element according to the present method, it is desirable that the alternating current applied between the electrodes of the appropriate cell has a rectangular waveform.

The present method may be practiced after the sensor is produced and before the sensor is actually used. Alternatively, the method may be applied to the sensing element, after the sensor is used for measuring the oxygen concentration of the external measurement gas, or at regular intervals during use of the sensor, so that the sensor accuracy is maintained at the desired level.

The second object indicated above may be achieved according to another aspect of the present invention, that is, by practicing the method described above to provide an oxygen concentration sensor whose sensing element has an improved structure capable of exhibiting excellent output characteristic or operating stability. The oxygen concentration sensor has a sensing element which includes an electrochemical oxygen pumping cell having an oxygen-ion conductive first solid electrolyte layer, and a first and a second electrode disposed on the first solid electrolyte layer, an electrochemical oxygen sensing cell having an oxygen-ion conductive second solid electrolyte layer and a third and a fourth electrode disposed on the second solid electrolyte layer, and diffusion-resistance means for introducing an external measurement gas under a predetermined diffusion resistance, for contact with the second and third electrodes. The first and second electrodes of the oxygen pumping cell and/or the third and fourth electrodes of the oxygen sensing cell consist of metal grains each having minute cracks on its surface. The minute cracks on the surfaces of the electrode metal grains provide a large number of triple contact points or active points among the introduced measurement gas, electrode metal and solid electrolyte, thereby assuring increased stability of electrochemical reaction of the electrochemical oxygen pumping cell and/or electrochemical oxygen sensing cell, and improving the consistency of measurement or operating stability of the oxygen concentration sensor.

For effective improvement in the output characteristic or operating stability of the sensor, it is preferable that both of the metal grains of the first and second electrodes of the oxygen pumping cell and the metal grains of the third and fourth electrodes of the oxygen sensing cell have the minute cracks on the surfaces.

BRIEF DESCRIPTION OF THE DRAWINGS

The above and optional objects, features and advantages of the present invention will be better understood by reading the following detailed description of a presently preferred embodiment of the invention, when considered in connection with the accompanying drawings, in which.

DETAILED DESCRIPTION OF THE PREFERRED EMBODIMENT

As described above, the principle of the present invention consists in applying a suitably determined alternating current to at least one of the oxygen pumping and sensing cells of the electrochemical sensing element of a double-cell type oxygen concentration sensor or detector, under a predetermined condition, for providing the sensing element with an improved structure, which permits the sensor to effect measurement of the oxygen concentration of a measurement gas, with highly consistent accuracy.

Figure 1:
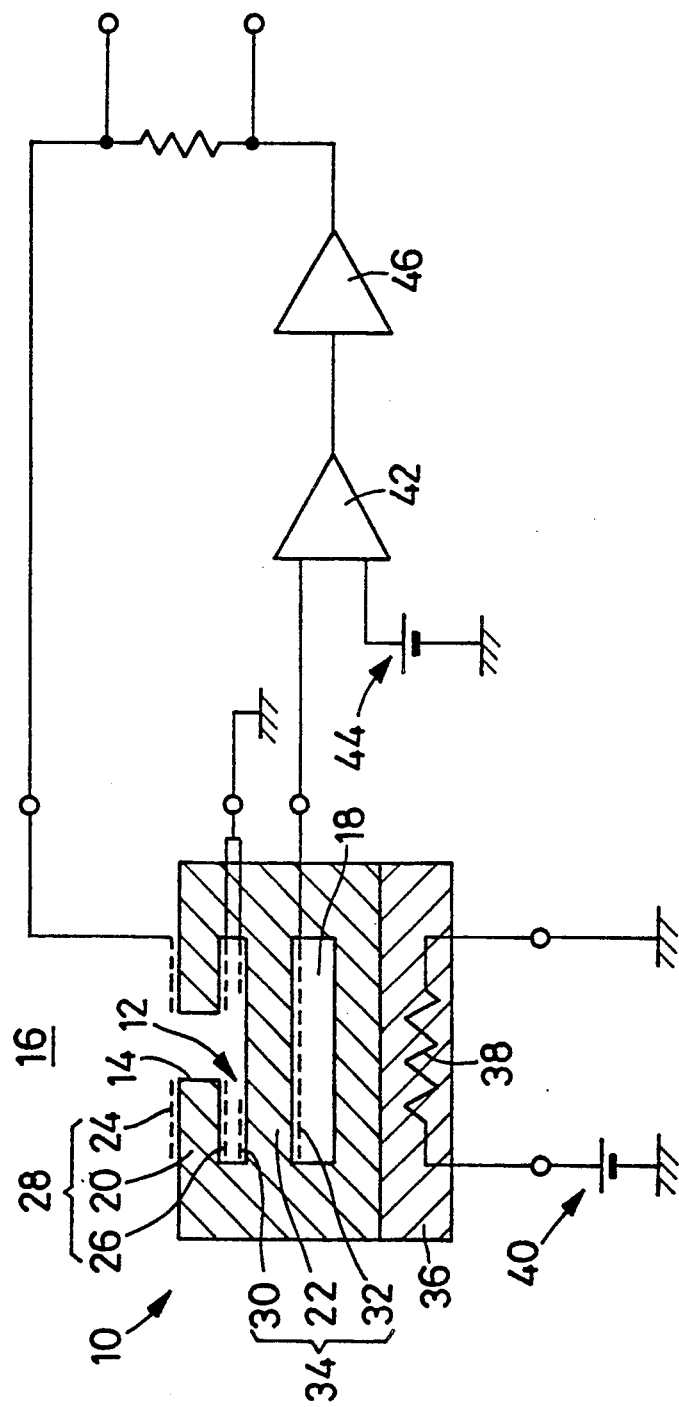
FIG. 1 is a schematic elevational view in cross section showing a basic arrangement of an oxygen concentration sensor to which the principle of the present invention is applicable.

Explained more specifically referring to FIG. 1 showing a basic arrangement of an oxygen concentration sensor to which the present invention may apply, reference numeral 10 denotes a sensing element of the sensor. The sensing element 10 has a generally elongate, planar, rectangular laminar structure including a plurality of co-fired layers of an oxygen-ion conductive solid electrolyte material such as zirconia ceramic. The sensing element 10 has diffusion-resistance means formed therein in the form of a round thin flat space 12, which has a predetermined resistance to diffusion of a gas therethrough. This internal thin flat space 12 is formed in parallel to the plane of the sensing element 10, i.e., to the opposite major surfaces of the element 10. The sensing element 10 also has a gas inlet aperture 14 in the form of a round hole which communicates with a central portion of the thin flat space 12, and with an external measurement-gas space 16 in which a measurement gas to be measured by the sensor exists. The measurement gas in the external space 16 is introduced into the thin flat space 12 through the gas inlet aperture 14. The sensing element 10 further has an air passage 18 independent of the thin flat space 12. The air passage 18 extends in the longitudinal direction of the element 10, and is open to the ambient air or atmosphere.

The sensing element 10 has a first solid electrolyte layer 20 through which the gas inlet aperture 14 is formed, and a second solid electrolyte layer 22 which cooperates with the first solid electrolyte layer 20 to define the thin flat space 12 therebetween. On the outer surface of the first solid electrolyte layer 20, there is formed a first electrode in the form of an annular outer pumping electrode 24 concentric with the gas inlet aperture 14. The outer pumping electrode 24 is formed such that the inner periphery is adjacent to the edge of the aperture 14. On the inner surface of the first solid electrolyte layer 20 which partially defines the round thin flat space 12, there is formed a second electrode in the form of an annular inner pumping electrode 26 which is concentric with and adjacent to the gas inlet aperture 14. The first solid electrolyte layer 20 and the outer and inner pumping electrodes 24, 26 constitute an electrochemical oxygen pumping cell 28.

On the surface of the second solid electrolyte layer 22 which partially defines the round thin flat space 12, there is formed a third electrode in the form of an annular measuring electrode 30 which is disposed concentrically with the inner pumping electrode 26 of the oxygen pumping cell 28. The mutually facing electrodes 26 and 30 define the thickness of the thin flat space 12. The second solid electrolyte layer 22 has the air passage 18, and a fourth electrode in the form of a reference electrode 32 formed on one of opposite surfaces defining the air passage 18, which one surface is nearer to the measuring electrode 30. The second solid electrolyte layer 22 and the measuring and reference electrodes 30, 32 constitute an electrochemical oxygen sensing cell 34.

The electrodes 24, 26, 30, 32 of the oxygen pumping and sensing cells 28, 34 are formed on the appropriate solid electrolyte layers 20, 22, by a suitable technique such as sputtering or plating, using a suitable known metallic material such as metals of the platinum group, which has a catalytic activity with respect to electrochemical reaction of oxygen. The electrodes may be formed of a cermet which is a mixture of a powder of a metal such as a metal of the platinum group, and a powder of a ceramic material such as zirconia, yttria or alumina. The electrode material applied to the solid electrolyte layers 20, 22 may be co-fired with the solid electrolyte layers. The fired electrodes 24, 26, 30, 32 may have a porous structure.

The sensing element 10 has an electrically insulating ceramic layer 36 formed as an integral part thereof, on one of opposite major surfaces of the solid electrolyte body 20, 22, which is remote from the outer pumping electrode 24. The ceramic layer 36 has a heat-generating element 38 embedded therein. The heat-generating element 38 is connected to an external power source 40, so that the element 38 to generates heat for maintaining the oxygen pumping and sensing cells 28, 34 at a suitable operating temperature.

The thus constructed sensing element 10 of the oxygen concentration sensor is operated as well known in the art. More specifically, the oxygen sensing cell 34 is connected to a differential amplifier 42, which compares an electromotive force induced by the sensing cell 34, with a reference voltage received from a reference voltage source 44. The differential amplifier 42 produces a voltage output proportional to a difference between the electromotive force and the reference voltage, which difference corresponds to the oxygen concentration of the atmosphere within the thin flat space 12. The voltage output is applied to a V/I converter 46, which converts the received voltage into the corresponding current having a positive or negative value. This current is applied as a pumping current to the oxygen pumping cell 28. As a result, the pumping cell 28 performs an oxygen pumping action for pumping oxygen from or into the thin flat space 12, so as to maintain the oxygen concentration within the thin flat space 12, at a predetermined level, for example, at the neutral or zero level. The pumping current applied to the pumping cell 28 to thus control the atmosphere within the thin flat space 12 represents the oxygen concentration of the measurement gas in the external measurement-gas space 16.

Figure 2:
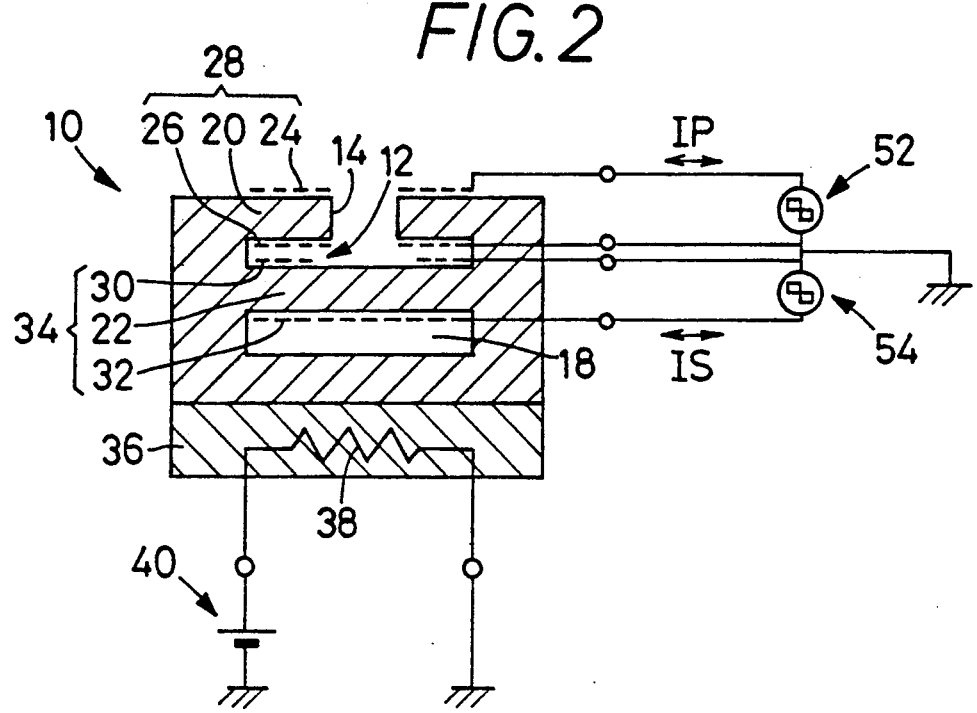
FIG. 2 is a schematic elevational view, illustrating a method of applying processing currents to oxygen pumping and sensing cells of the sensor of FIG. 1 according to the present invention.

To improve the operating stability or output characteristic of the sensing element 10, processing currents $I_p$ and $I_s$ are applied to the oxygen pumping and sensing cells 28, 34, respectively, as shown in FIG. 2, according to one embodiment of the present invention. To this end, an AC power source 52 is connected between the outer and inner pumping electrodes 24, 26 of the pumping cell 28, while another AC power source 54 is connected between the measuring and reference electrodes 30, 32 of the sensing cell 34. However, one of the two power sources 52, 54 may be eliminated.

Figure 3:
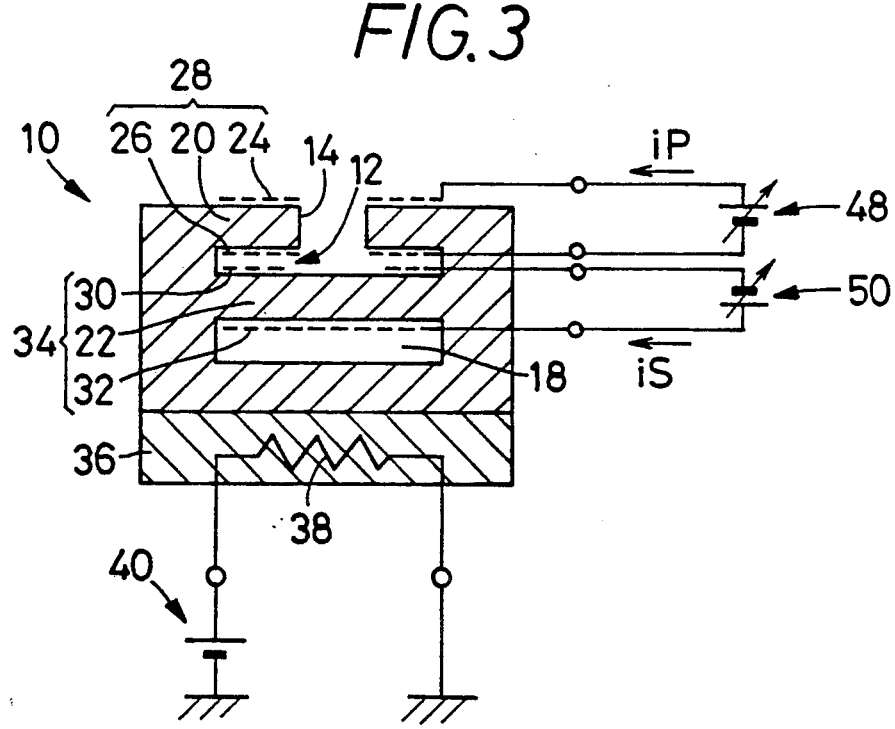
FIG. 3 is a schematic view indicating an example of a manner in which the polarographic limit currents of the cells are measured.

The values of the alternating currents $I_p$ and $I_s$ as the processing currents are determined based on polarographic limit current values $i_{PL}$, $i_{SL}$ of the corresponding oxygen pumping and sensing cells 28, 34, respectively. The polarographic limit current values $i_{PL}$ and $i_{SL}$ can be measured by a known method. For instance, a variable DC voltage source 48 is connected between the outer and inner pumping electrodes 24, 26 of the cell 28, as shown in FIG. 3, so that a pump current $i_P$ is applied between the electrodes 24, 26. A saturation level of the pump current $i_P$ based on the velocity of diffusion of oxygen molecules through the thin flat space 12 is determined by measuring the pump current $i_P$ in relation to a pump voltage $v_P$ applied between the two electrodes 24, 26. The polarographic limit current value $i_{PL}$ is equal to the determined saturation level of the pump current $i_P$. Similarly, a variable DC voltage source 50 is connected between the measuring and reference electrodes 30, 32, to apply a pump current $i_S$ between the electrodes 30, 32. A saturation level of the pump current $i_S$ based on the velocity of diffusion of the oxygen molecules through the thin flat space 12 is determined by measuring the pump current $i_S$ in relation to a pump voltage $v_S$ applied between the electrodes 30, 32. The polarographic limit current value $i_{SL}$ is equal to the determined saturation level of the pump current $i_S$. Since the polarographic limit current values $i_{PL}$ and $i_{SL}$ vary with the temperature of the sensing element 10 and the atmosphere within the thin flat space 12, and other conditions in which the limit current values $i_{SL}$, $i_{PL}$ are measured. Therefore, the conditions in which the limit current values $i_{SL}$, $i_{PL}$ are measured should be substantially the same as the conditions in which the alternating currents $I_p$ and $I_s$ are applied to the pumping and sensing cells 28, 34, to process the sensing element 10 according to the present invention.

The alternating currents $I_p$ and $I_s$ are determined by the thus measured polarographic limit current values $i_{PL}$ and $i_{SL}$, respectively, such that the alternating currents $I_p$, $I_s$ are selected within a range defined by a lower limit equal to the limit current values $i_{PL}$, $i_{SL}$, and an upper limit which is five times as large as the limit current values $i_{PL}$, $i_{SL}$. Namely, the alternating current values $I_p$, $I_s$ are 1–5 times as large as the respective polarographic limit current values $i_{PL}$, $i_{SL}$. Preferably, the alternating current values $I_p$, $I_s$ are 2–3 times as large as the limit current values $i_{PL}$, $i_{SL}$. If the values $I_p$, $I_s$ are lower than the values $i_{PL}$, $i_{SL}$, the desired improvement of the sensing element 10 cannot be obtained by the application of the alternating currents $I_p$, $I_s$. If the alternating currents $I_p$, $I_s$ exceed the values five times as large as the limit current values $i_{PL}$, $i_{SL}$, the solid electrolyte layers 20, 22 are subjected to excessive reduction, and tend to be deteriorated.

The AC power sources 52, 54 for applying the alternating currents $I_p$, $I_s$ as the processing currents to the sensing element 10 are preferably adapted such that the alternating currents $I_p$, $I_s$ have a rectangular waveform having a constant amplitude. If direct currents whose values exceed the polarographic limit current values are applied to the pumping and sensing cells 28, 34, the solid electrolyte layers 20, 22 are deteriorated.

If the frequency of the alternating currents $I_p$, $I_s$ is excessively high, the processing of the sensing element 10 by the currents $I_p$, $I_s$ is adversely influenced by the electrostatic capacity of the electrodes 24, 26, 30, 32. In view of this, the frequency of the alternating currents $I_p$, $I_s$ supplied by the AC power sources 52, 54 should be 10 Hz or lower, preferably within a range of 0.1-1 Hz.

When the alternating currents $I_p$, $I_s$ are applied to the sensing element 10, the heat-generating element 38 is energized by the external heater power source 40, so as to maintain the sensing element 10 at 600° C. or higher. If the temperature of the sensing element 10 during application of the alternating currents $I_p$, $I_s$ is lower than 600° C., the catalytic activities of the metallic material of the electrodes 24, 26, 30, 32 may be lowered, and the solid electrolyte layers 20, 22 may be deteriorated due to ion dissociation. While the upper limit of the heating temperature varies with the materials of the sensing element 10, the upper limit is preferably 1200° C. or lower, where the electrodes 24, 26, 30, 32 are formed of a zirconia-platinum cermet while the solid electrolyte layers 20, 22 are formed of zirconia.

A suitable duration for which the alternating currents $I_p$, $I_s$ are applied to the sensing element 10 varies with the values of the currents. Usually, the currents $I_p$, $I_s$ are continuously applied for at least one minute, preferably about 30 minutes.

The application of the alternating currents $I_p$, $I_s$ is effected while the sensing element 10 is placed in a controlled atmosphere, usually in the ambient air, which is relatively easy to control.

The processing of the sensing element 10 by applying the alternating currents $I_p$, $I_s$ to the cells 28, 34 may be effected after the sensor is manufactured and before it is actually used, or alternatively after the sensor is actually used for measuring the oxygen concentration of the measurement gas. The processing may be conducted at regular intervals during use of the sensor.

Figure 4:
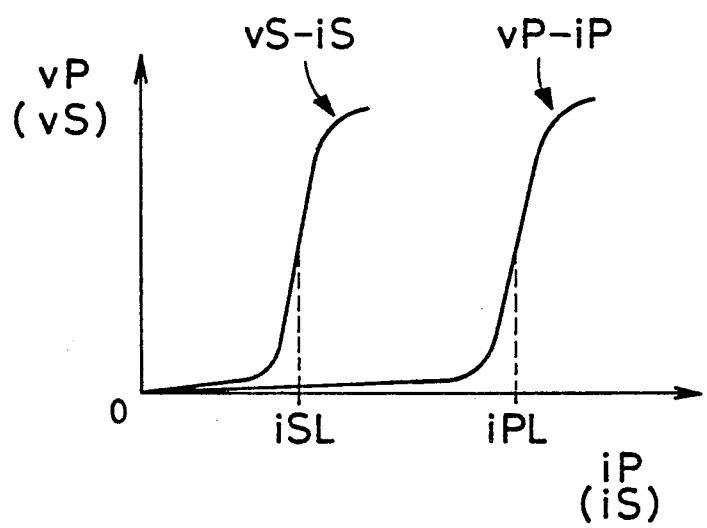
FIG. 4 is a graph showing voltage-current relationships of the cells processed by the processing currents as indicated in FIG. 2, in relation to the limit current values measured as indicated in FIG. 3.

While the illustrated embodiment of FIG. 2 is adapted to apply the processing alternating currents $I_p$, $I_s$ to both of the oxygen pumping and sensing cells 28, 34, respectively, the principle of the invention requires at least one of the cells 28, 34 to be processed by the corresponding processing current $I_p$, $I_s$. The sensor whose cells 28, 34 were processed by the alternating currents $I_p$, $I_s$ were tested with a voltage $v_P$ applied between the pumping electrodes 24, 26 and a voltage $v_S$ applied between the measuring and reference electrodes 30, 32. The graph in FIG. 4 shows the voltage $i_P$ in relation to a current $i_P$ flowing between the electrodes 24, 26 of the pumping cell 28, and the voltage $v_S$ in relation to a current $i_S$ flowing between the electrodes 30, 32 of the sensing cell 34. The relationships $v_P-i_P$ and $v_S-i_S$ are considerably stabilized, with effectively reduced influences by the temperature of the solid electrolyte layers 20, 22 and by CO and $H_2O$ in the atmosphere introduced into the thin flat space 12. Thus, the test showed a considerable improvement in the output consistency or operating stability (stability in measuring accuracy).

It appears that the improved stability of the $v_P-i_P$ output characteristic of the pumping cell 28 and the $v_S-i_S$ output characteristic of the sensing cell 34 are derived from the processing by the alternating currents $I_p$, $I_s$ described above, which results in a structural improvement at the interface between the metal grains or particles of the electrodes 24, 26, 30, 32 and the solid electrolyte layers 20, 22.

Figure 5:
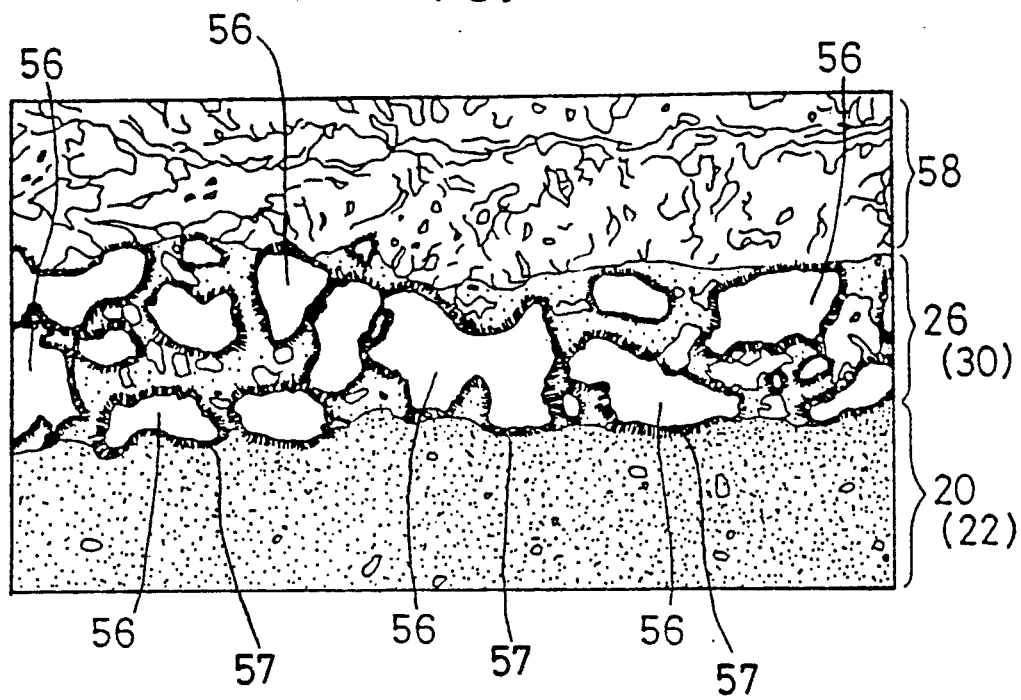
FIG. 5 is a fragmentary microscopic illustration of a part of the processed cell, showing in cross section the structure of an electrode of the cell.

More specifically, an observation by an electron microscope of a cut surface of the sensing element 10 processed as described above indicates that each metal grain 56 of each electrode 24, 26, 30, 32 is given a multiplicity of minute or micro cracks 57 on its surface, as indicated in FIG. 5. The minute cracks 57 have depths of about 0.1-1 $\mu$m, and the sum of the widths of the cracks 57 is equal to at least 50% of the length of the outline of the metal grain 56, as seen in the cross sectional view taken by an electron microscope.

The minute cracks 57 formed on the surface of each metal grain 56 of the electrodes provide a large number of active points, i.e., points of triple contact among the measurement gas, metal of the electrodes and solid electrolyte, which contribute to an electrochemical reaction of oxygen, whereby the operating stability of the sensing element 10 as a whole can be maintained at a sufficiently high level.

EXAMPLE

An example of the method for processing a sensing element of an oxygen concentration sensor according to the invention, and the thus processed sensing element will be described in detail.

The sensing element 10 processed in the present example is constructed as shown in FIG. 1. The first and second solid electrolyte layers 20, 22 were formed of zirconia, while the electrodes 24, 26, 30, 32 of the pumping and sensing cells 28, 34 were each formed of a cermet consisting of platinum and zirconia.

The polarographic limit current value $i_{PL}$ measured between the outer and inner electrodes 24, 26 of the pumping cell 28 in the manner described above was 5 mA, while the polarographic limit current value $i_{SL}$ measured between the measuring and reference electrodes 30, 32 was 0.5 mA. The measurements of these limit current values $i_{PL}$, $i_{SL}$ were effected under the same condition as used for applying the processing currents to the sensing element 10. That is, the sensing element 10 was placed in the ambient air and maintained at a temperature of 900°-1000° C., with the heat-generating element 38 connected to the external 16 V power source 40.

The alternating current $i_{PL}$ having a 0.5 Hz rectangular waveform and an amplitude of ±15 mA (3 times the corresponding polarographic limit current value $i_{PL}$) was applied between the outer and inner pumping electrodes 24, 26 of the pumping cell 28, while at the same time the alternating current $i_{SL}$ having a 0.5 Hz rectangular waveform and an amplitude of ±1.5 mA (also 3 times the corresponding polarographic limit current value $i_{SL}$) was applied between the measuring and reference electrodes 30, 32 of the sensing cell 34. The application of these alternating currents $i_{PL}$, $i_{SL}$ was continued for 30 minutes to terminate the processing of the sensing element 10.

As indicated above, the alternating currents $i_{PL}$, $i_{SL}$ were applied while the first and second solid electrolyte layers 20, 22 were placed in the ambient air and kept at 900°-1000° C., with the heat-generating element 38 connected to the external 16 V power source 40.

Figure 6:
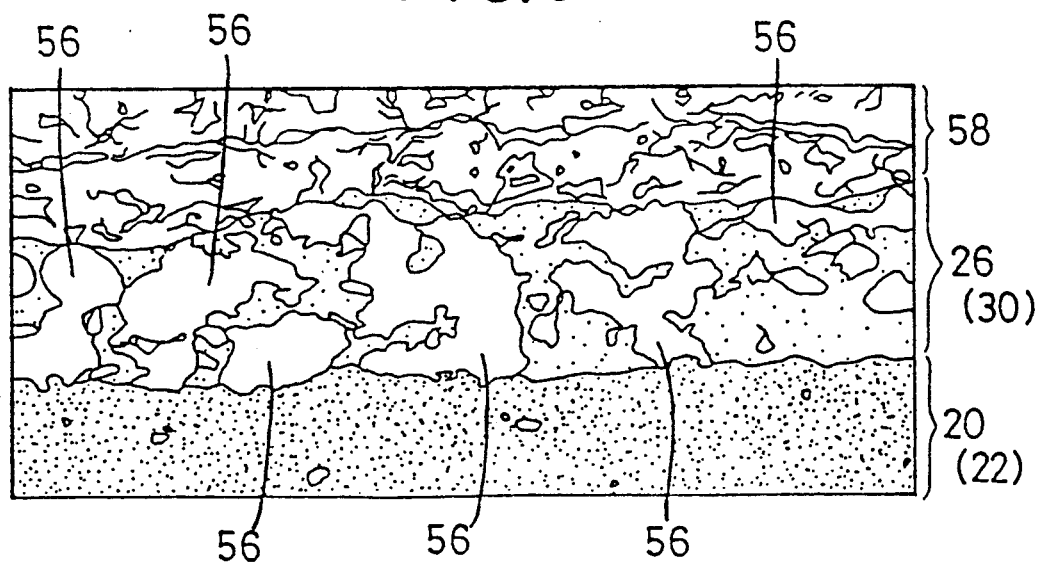
FIG. 6 is a fragmentary microscopic illustration of a conventional non-processed cell, showing a part corresponding to that shown in FIG. 5.

A microscopic observation of a cut surface of the thus processed pumping and sensing cells 28, 34 adjacent to the thin flat space 12 indicated the presence of a multiplicity of minute or micro cracks 57 on the surface of each metal grain 56 of the electrodes 26, 30 on the surfaces of the solid electrolyte layers 20, 22 which define the thin flat space 12, as illustrated in FIG. 5. Reference numeral 58 in FIG. 5 designates a porous alumina layer which protects the electrode 26, 30. For comparison, FIG. 6 illustrates a cut surface of the corresponding parts of the cells 28, 34 of the non-processed sensing element 10, as observed by an electron microscope. The illustration of FIG. 6 indicates that none of the metal grains 56 of the electrodes 26, 30 has minute cracks as indicated at 57 in FIG. 5.

It will be understood from the above description by reference to FIGS. 5 and 6 that the sensing element 10 having the processed cells 28, 34 whose metal grains 56 of the electrodes 26, 30 have the minute cracks 57 is given an improved interface between the electrodes 26, 30 and the solid electrolyte layers 20, 22, that is, provided with a large number of points of triple contact among the measurement gas, electrode metal and solid electrolyte. Accordingly, the electrochemical reaction of the oxygen pumping and sensing cells 28, 34 is enhanced, enabling the sensing element 10 to assure effectively improved consistency in the output characteristic or effectively improved stability in measuring accuracy.

The $v_P$–$i_P$ characteristic of the electrodes 24, 26 of the pumping cell 28 and the $v_S$–$i_S$ characteristic of the electrodes 30, 32 of the sensing cell 34 were detected at several different times under the same condition, on each of the processed and non-processed specimens of the sensing element 10. While the variation or fluctuation of the characteristics was as large as 3% on the non-processed specimen, the variation on the processed specimen was reduced to 1% or less.

Another test was conducted to see the influences of the temperature change on the above $v_P$–$i_P$ and $v_S$–$i_S$ characteristics of the processed and non-processed specimens. In the test, the temperature of the solid electrolyte layers 20, 22 was changed by 50° C. The test showed as large as 10% fluctuation of the characteristics on the non-processed specimen, but as small as 5% fluctuation of the same on the processed specimen. The test also showed a relatively small difference in the amount of fluctuation of the characteristics, among the individual specimens of the processed sensing element 10.

A further test was conducted on the processed and non-processed specimens while they were exposed to a measurement gas containing CO and $H_2O$ which easily adhere to the sensing element 10. The test revealed a less variation in the $v_P$–$i_P$ and $v_S$–$i_S$ characteristics on the processed specimen than on the non-processed specimen. Further, the processed specimen suffered less sintering of the electrodes at a high temperature, and a comparatively reduced change in the output current $i_P$, $i_S$ due to the sintering. This means improved durability of the processed sensing element 10.

It will be understood that the method of the present invention for processing the sensing element 10 is effective to increase the stability of the $v_P$–$i_P$ and $v_S$–$i_S$ characteristics of the pumping and sensing cells 28, 34, and is consequently effective to improve the operating characteristic of the oxygen concentration sensor equipped with the electric control circuit as shown in FIG. 1. Namely, the present method is effective to increase the stability of the voltage output of the sensing cell 34, i.e., the accuracy of the voltage output which is indicative of the oxygen concentration of the measurement gas, and increase the stability of the pumping current which is applied to the pumping cell 28 based on the voltage output of the cell 34, i.e., the accuracy of the pumping current which eventually represents the oxygen concentration of the measurement gas. Further, the present method effectively reduces the adverse influences of the temperature change and CO and $H_2O$ on the output of the sensor, and the output accuracy variation between the individual sensors. Thus, the present method permits the oxygen concentration sensor to exhibit enhanced consistency and stability in the output characteristic and measuring accuracy.

While the method of processing a sensing element of an oxygen concentration cell, and the processed sensing element have been described in detail in connection with the presently preferred embodiment of the present invention, it is to be understood that the invention is not limited to the details of the illustrated embodiment, but may be embodied with various changes, modifications and improvements, which may occur to those skilled in the art, without departing from the spirit of the present invention.

For instance, the construction of the oxygen concentration sensor to which the present invention is applicable is not limited to that which has been described by reference to the drawings. That is, the principle of the present invention is applicable to any configuration of the double-cell type oxygen sensor including an oxygen pumping cell, an oxygen sensing cell and diffusion-resistance means. For example, the gas inlet aperture 14 and the round thin flat space 12 may be replaced by an orifice or hole having a very small diameter which is formed so as to function as the diffusion-resistance means for introducing the external measurement gas, under a predetermined diffusion resistance, for contact with the electrodes 26 and 30 (second and third electrodes) of the sensing element 10.

The processing current applied between the electrodes 24, 26 of the pumping cell 28 and/or between the electrodes 30, 32 of the sensing cell 34 is not limited to the alternating current having a rectangular or square waveform. The processing alternating current may have a sine, sawtooth or triangular wave, or any pulse wave. In the case of a sine wave current or similar alternating current, the peak value is determined to be 1–5 times as large as the determined polarographic limit current value of the corresponding cell 28, 34.

The processing of the sensing element 10 may be effected while the element 10 is placed in a controlled atmosphere other than the ambient air. In this case, the direction of flow of the polarographic limit currents of the pumping and sensing cells 28, 34 may be reversed with respect to that where the processing is effected in the ambient air.

As indicated above, an advantage of the present invention may be more or less provided even if the processing alternating current is applied to only one of the oxygen pumping and sensing cells 28, 34.

What is claimed is:

1. A method of processing a sensing element of an oxygen concentration sensor including an electrochemical oxygen pumping cell having an oxygen-ion conductive first solid electrolyte layer, and a first and a second electrode disposed on said first solid electrolyte layer, an electrochemical oxygen sensing cell having an oxygen-ion conductive second solid electrolyte layer and a third and a fourth electrode disposed on said second solid electrolyte layer, and diffusion-resistance means for introducing an external measurement gas under a predetermined diffusion resistance, for contact with said second and third electrodes, comprising a step of:

applying an alternating current having a frequency of not higher than 10 Hz to said oxygen pumping cell of said sensing element, through said first and second electrodes, while said sensing element is held at a temperature not lower than 600° C., said alternating current being 1-5 times as large as a polarographic limit current value of said pumping cell.

2. A method according to claim 1, wherein said alternating current is applied to said oxygen pumping cell while said sensing element is placed in the air.

3. A method according to claim 1, wherein said alternating current has a rectangular waveform.

4. A method according to claim 1, wherein said alternating current is applied to said oxygen pumping cell, after said oxygen concentration sensor has been used for measuring an oxygen concentration of said external measurement gas.

5. A method of processing a sensing element of an oxygen concentration sensor including an electrochemical oxygen pumping cell having an oxygen-ion conductive first solid electrolyte layer, and a first and a second electrode disposed on said first solid electrolyte layer, an electrochemical oxygen sensing cell having an oxygen-ion conductive second solid electrolyte layer and a third and a fourth electrode disposed on said second solid electrolyte layer, and diffusion-resistance means for introducing an external measurement gas under a predetermined diffusion resistance, for contact with said second and third electrodes, comprising a step of:

applying an alternating current having a frequency of not higher than 10 Hz to said oxygen sensing cell of said sensing element, through said third and fourth electrodes, while said sensing element is held at a temperature not lower than 600° C., said alternating current being 1-5 times as large as a polarographic limit current value of said sensing cell.

6. A method according to claim 5, wherein said alternating current is applied to said oxygen sensing cell while said sensing element is placed in the air.

7. A method according to claim 5, wherein said alternating current is applied to said oxygen sensing cell, after said oxygen concentration sensor has been used for measuring an oxygen concentration of said external measurement gas.

8. A method of processing a sensing element of an oxygen concentration sensor including an electrochemical oxygen pumping cell having an oxygen-ion conductive first solid electrolyte layer, and a first and a second electrode disposed on said first solid electrolyte layer, an electrochemical oxygen sensing cell having an oxygen-ion conductive second solid electrolyte layer and a third and a fourth electrode disposed on said second solid electrolyte layer, and diffusion-resistance means for introducing an external measurement gas under a predetermined diffusion resistance, for contact with said second and third electrodes, comprising a step of:

applying an alternating current having a frequency of not higher than 10 Hz to said oxygen pumping cell of said sensing element through said first and second electrodes, and concurrently to said oxygen sensing cell of said sensing element through said third and fourth electrodes, while said sensing element is held at a temperature not lower than 600° C., said alternating current being 1-5 times as large as a polarographic limit current value of the corresponding one of said pumping and sensing cells.

9. A method according to claim 8, wherein said alternating current is applied to said oxygen pumping and sensing cells while said element is placed in the air.

10. A method according to claim 8, wherein said alternating current is applied to said oxygen pumping and sensing cells, after said oxygen concentration sensor has been used for measuring an oxygen concentration of said external measurement gas.

* * * * *